United States Patent [19]
Stemmler et al.

[11] 4,379,016
[45] Apr. 5, 1983

[54] METHOD AND DEVICE FOR APPLYING ELASTIC STRIPS IN SECTIONS ONTO A WEB OF MATERIAL USED FOR MAKING DIAPERS

[75] Inventors: Kurt Stemmler, Neuwied; Heinrich Metheisen, Rengsdorf, both of Fed. Rep. of Germany

[73] Assignee: Winkler + Dunnebier Maschinefabrik und Eisengiesseret GmbH & Co. KG, Neuwied, Fed. Rep. of Germany

[21] Appl. No.: 254,015

[22] Filed: Apr. 13, 1981

[30] Foreign Application Priority Data

Apr. 26, 1980 [DE] Fed. Rep. of Germany ....... 3016197

[51] Int. Cl.³ ..................... A61F 13/16; B32B 31/04
[52] U.S. Cl. .................................. 156/205; 118/44; 156/164; 156/244.22; 156/471; 156/474; 264/167; 427/275
[58] Field of Search ........ 156/164, 205, 201, 471–474, 156/244.22, 244.15, 244.27, 470, 292, 138, 140, 244.11; 427/275; 118/44; 264/167; 128/288, 290 R

[56] References Cited

U.S. PATENT DOCUMENTS

| | | | |
|---|---|---|---|
| 2,235,682 | 3/1941 | Hawley | 156/164 |
| 2,674,299 | 4/1954 | Bruker | 156/205 |
| 3,773,590 | 11/1973 | Morgan | 156/244.27 |
| 3,837,973 | 9/1974 | Asakura et al. | 156/473 |
| 3,904,473 | 9/1975 | Warner et al. | 156/470 |
| 4,081,301 | 3/1978 | Buell | 156/164 |
| 4,227,952 | 10/1980 | Sabee | 156/164 |
| 4,285,747 | 8/1981 | Rega | 156/164 |
| 4,297,157 | 10/1981 | Van Uliet | 156/164 |

*Primary Examiner*—Jerome W. Massie
*Attorney, Agent, or Firm*—Allison C. Collard; Thomas M. Galgano

[57] ABSTRACT

A method for mounting elastic strips onto a web of material for making diapers or the like, includes the steps of gathering-up the web of material, i.e., it is shortened by forming a multiplicity of fine transverse folds thereon, and mounting unstretched elastic strips in discrete sections onto the edge areas of the gathered-up web of material. A device for carrying out the method is also provided which includes a drum having a toothed gear-like surface, an embossing roller having a toothed gear-like surface which is in camming engagement with the drum, a device for holding and guiding the gathered-up web of material on the drum and a station for mounting elastic strips in discrete sections onto the edge areas of the web of material which is held and guided on the drum.

13 Claims, 4 Drawing Figures

METHOD AND DEVICE FOR APPLYING ELASTIC STRIPS IN SECTIONS ONTO A WEB OF MATERIAL USED FOR MAKING DIAPERS

The invention relates to a method for sectionally mounting elastic strips onto a web of material for making diapers or the like and to a device suitable for carrying out the method. More particularly, it relates to such a method and device for mounting these elastic strips in the areas of the web of material which encompass the legs of the wearer after the diaper has been finished.

Commonly-made diapers are made of a support web of material which, in itself, has a very limited inherent elastic and plastic deformability. Consequently, the afforded deformability is not sufficient to assume a safe engagement and thereby a sealing of the diapers around the thighs of the wearer.

It has therefore previously been proposed to mount a rubber ribbon in the leg area of the diaper which could be sewed into or bonded onto the diaper in this leg area. U.S. Pat. No. 4,081,301 (which issued to Kenneth Buell) discloses such a method and a suitable device for carrying out the method.

In particular, Buell proposed to combine a continuously moving stretched rubber ribbon, which may be drawn off from a roll, with a continuously moving web of material of which the diapers are made of, thus bonding the rubber ribbon onto the web of material in the area of the web of material requiring a high degree of elasticity—namely, in the leg area of the wearer. Consequently, the bonding area is broken up into a plurality of discrete bonding spots. After the further layers of the diaper, e.g., the absorbent insert and the cover layer, are mounted onto the rubber ribbon-bonded web of material, the created finished endless web of diaper material is separated into individual diapers by means of a transverse cutting means. As a result, the rubber ribbons contract which, in the area in which they are bonded with the diaper, results in a forming of folds or gathering up of the diapers, thus resulting in the desired high elasticity in the leg area.

This briefly described method in accordance with Buell is disadvantageous in various aspects. First of all, it is very expensive to constantly supervise the stretching of the rubber ribbon by controlling it by means of control elements. Secondly, it is not so easy to provide a spotwise bonding of the rubber ribbon on the web of material. However, the most severe disadvantage of the method in accordance with Buell is that it is combined with a high consumption of rubber ribbons. The rubber ribbons in accordance with Buell are as long as the web of material. However, to attain the object of the invention—namely, to increase the elasticity in the leg area of the diaper, one actually needs only to provide as much rubber ribbon as is required by the leg area of the diaper.

It is therefore an object of the invention to provide a method and a suitable device for carrying out this method which does not require a stretching of the rubber ribbon before mounting it on the web of material, wherein the manufacturing involved in effecting the connection between the elastic strip and the web of material is carried out in a simple manner, and whereby the material consumption is reduced to a minimum.

This object is obtained according to the invention by initially gathering-up the web of material, i.e., it is shortened by forming fine transverse pleats or folds, and then mounting or applying relaxed or unstretched elastic strips in sections onto the edge areas of the gathered-up web of material.

This object of the invention is advantageous in that no devices are required for supervising and controlling the stretching of an elastic element. Moreover, the requirement that these elastic premanufactured elements be mounted in a spotwise manner, in the form of strips onto the webs of material, is facilitated by the fact that the elastic strips are already in a spotwise contact with the material, due to the formation of the folds thereon. Furthermore, it should be noted that only as much elastic material is used which is required to cover the areas requiring a high degree of elasticity.

In a further embodiment of the invention, instead of a prefabricated elastic strip, a strip of moldable or sprayable liquid material is applied onto the areas of the gathered-up web of material. As the liquid material for forming the elastic strips, one should use such materials which assume a rubber-like elastic consistency after cooling or after a very rapid drying time.

It is a further object of the invention to provide a device for carrying out the method.

This further object of the invention is obtained by the provision of a device having a drum with a toothed gear-like surface and an embossing roller having the same surface as the drum which is in camming engagement therewith. The device further includes means for holding and guiding the gathered-up web of material on the drum, and a station for a sectionally mounting elastic strips onto the edge areas of the web of material which is present on the drum.

In a further embodiment of the invention, the station for mounting the elastic strip is designed as a spray or casting device.

In a particularly simple embodiment of the inventive device, the tooth gear-like surface of the drum, as well as the surface of the embossing roller is provided by toothed gear belts, whereby the toothed gear belt which forms the toothed gear-like surface of the embossing roller is guided around the embossing roller, as well as a large part of the drum—namely, the part of the drum around which the web of material is guided.

Thereby, in a simple manner, this toothed gear belt which travels around both rollers not only acts as an embossing tool but, at the same time, holds the web of material in a meander-like or serpentine gathered-up manner in a snug engagement against the surface of the drum.

The aforementioned toothed gear belts may be designed as two wide belts or a plurality of small adjacent toothed bear belts. However, it is important to make sure that a small free area for mounting the elastic strip material on the gathered-up web of material is provided.

Other objects and features of the present invention will become apparent from the following detailed description when taken in connection with the accompanying drawings which disclose several embodiments of the invention. It is to be understood that the drawings are designed for the purpose of illustration only and are not intended as a definition of the limits of the invention.

In the drawings, wherein similar reference characters denote similar elements throughout the several views.

Figure 1:
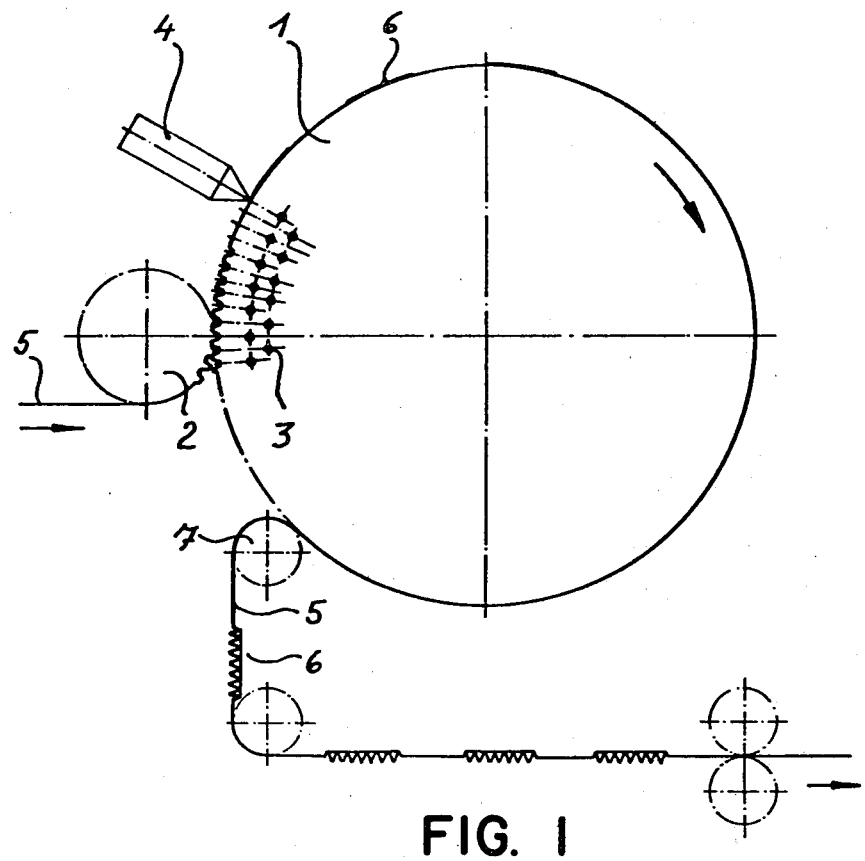
FIG. 1 is a schematically-illustrated side view of a device embodying the present invention.

Referring now in detail to the drawings and, in particular FIG. 1 thereof, the major component of the device is a drum 1 which as shown in the drawing has a tooth gear-like outer surface. An embossing roller 2 with the same type of outer surface is in camming engagement therewith. Drum 1 is provided with a plurality of vacuum bores 3 which are coupled with a vacuum power source by means of control devices (not shown). A station 4 for effecting a sectional mounting of the elastic strips is provided above drum 1. This station is designed as a spray device having a spray nozzle above each of the edge areas of the web of material 5 which travels around drum 1.

The mode of operation of the device as described relative to its fundamental components is as follows.

The web of material 5 is introduced into the slot between drum 1 and embossing roller 2 and is folded or pleated in a meander-like fashion between the teeth of these two rollers. Due to the vacuum applied through the vacuum bores 3, the web of material 5 is held in tight engagement against the surface of drum 1 after leaving the roller slot. The web is guided beneath station 4 for mounting the elastic strip. This station 4 sprays a heated liquid material which is controlled by control means (not shown), in dependency on the machine speed, in a sectional or discrete manner in the form of small strips 6 onto the edge portions of the gathered-up web of material 5 and, after hardening, the liquid material assumes a rubber elastic consistency.

During the further movement of the drum, the heat is withdrawn from the liquid material mainly due to the large mass of drum 1. After a certain length of travel, which is sufficient for cooling, the vacuum supply to the vacuum bores 3 is interrupted by the control means (not shown), and the web of material is removed from the drum by means of a deflection roller 7 and is fed to a further processing machine.

Figure 2:
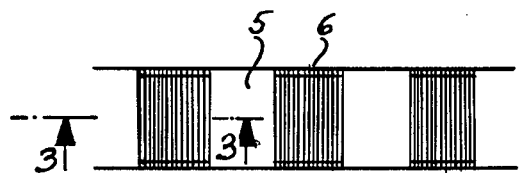
FIG. 2 is a plan view of the web of material after leaving the device shown in FIG. 1.

The slight tension which is exerted on the web of material results in that the gathered-up material in the areas in which no elastic material is needed is again restored to its original shape so that, as shown in FIG. 2, after it leaves the machine, the web of material consists of alternating continuous smooth non-elastic and gathered-up elastic areas.

Figure 3:
FIG. 3 is a sectional view through the web of material taken along line 3—3 of FIG. 2.

FIG. 3 is merely an enlarged partial sectional view through one of the gathered-up areas provided with elastic strips in accordance with FIG. 2. It is shown therein that the liquid material sprayed onto the web of material 5 which acts as the elastic strip 6, extends deeply into the base of the folds of the web of material 5.

Figure 4:
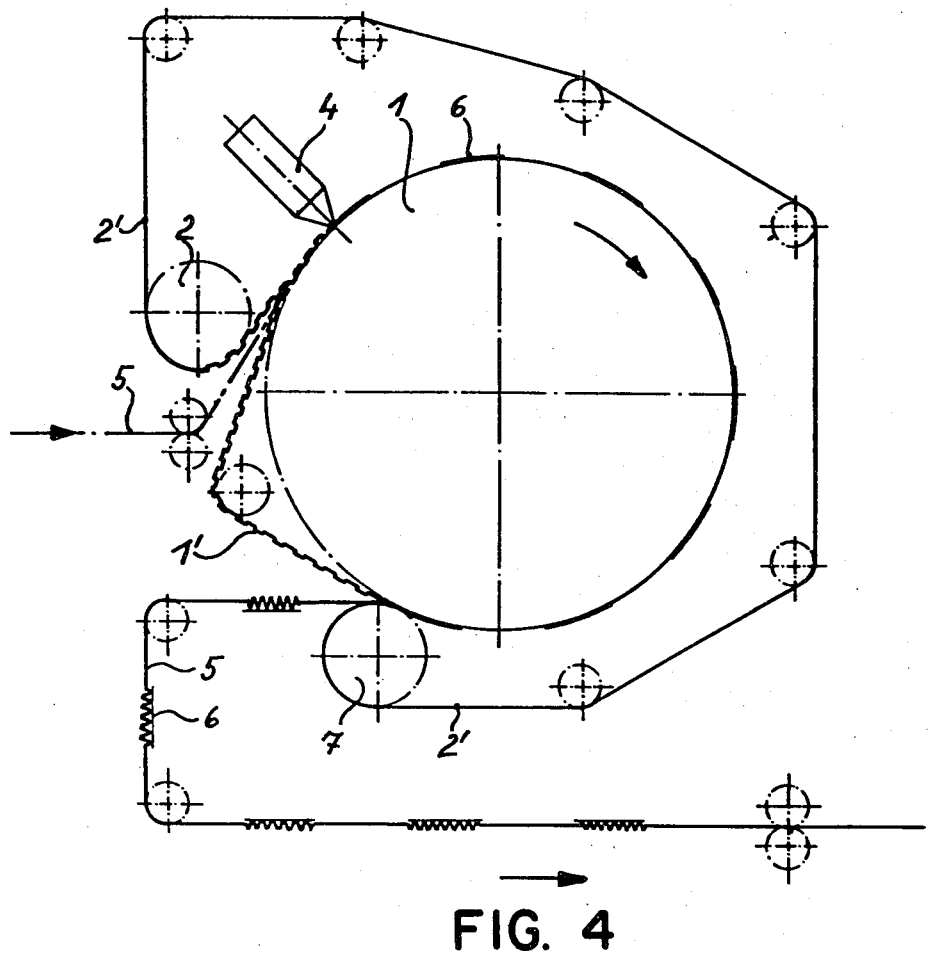
FIG. 4 is a schematically-illustrated side view of a further device embodying the present invention.

FIG. 4 shows a further embodiment of the device, comparable to that shown in FIG. 1. This embodiment basically consists of a drum 1, an embossing roller 2 and a station 4 disposed above drum 1 for applying elastic strips 6, as also shown in FIG. 1. In contrast to the previously-described embodiment, the surfaces of drum 1 and embossing roller 2 are smooth. The tooth gear-like surfaces is obtained by "reversely" mounted tooth gear belts 1', 2', i.e., the teeth are projected outwardly. The tooth gear belt 2' does not only extend around the embossing roller 2 but it also extends around a large part of the drum. Thereby, as will be shown in the following description of the mode of operation, it does not only function as an embossing tool but it also assumes the function of the vacuum bores 3 shown in FIG. 1., i.e., it also acts to hold the gathered-up web of material 5 on the surface of the drum.

This embodiment of the invention which is briefly described with respect to its basic or fundamental operating components operates as follows:

The web of material 5 is fed into the slot between tooth gear belts 1', 2' which run together on drum 1 and the web is folded or pleated in a meander-like manner between the intertwining teeth. The web of material is held in its gathered-up condition by the tooth gear belt 2' which also runs on drum 1. The web of material 5 is then fed beneath station 4 and it is provided with elastic strips 6 in the end areas thereof, as previously described. After a further length of travel which is sufficient for the elastic strip 6 to harden, the web of material 5 as well as the tooth gear belt 2' are removed from the drum 1, by means of a deflection roller 7. The tooth gear belt 2' is returned to the embossing roller 2 by means of further deflection rollers and the web of material is fed to a further machine (not shown) for further processing.

Thus, while only several embodiments of the present invention have been shown and described, it will be obvious that many changes and modifications may be made thereunto, without departing from the spirit and scope of the invention.

What is claimed is:

1. A method for mounting elastic strips in discrete sections onto a web of material for making diapers, comprising the steps of:

gathering-up a web of material by forming a multiplicity of fine transverse folds therein; and mounting unstretched elastic strips longitudinally, relative to the web, in discrete sections onto the edge areas of said gathered-up web of material, such that said strips are each affixed at least at discrete points along the total unstretched length thereof to said folds in contact therewith, so as to produce a web having, in the longitudinal direction thereof, alternating relatively continuous, smooth and non-elastic areas and gathered-up, relatively elastic areas.

2. The method according to claim 1, wherein said mounting step comprises mounting segments of a prefabricated elastic ribbon onto said gathered-up web of material.

3. The method according to claim 1, wherein said mounting step comprises spraying a liquid material onto said web of material which, when it hardens, forms said elastic strips.

4. The method according to claim 1, wherein said mounting step comprises casting a liquid material onto said web of material which, when it hardens, forms said elastic strips.

5. A device for mounting elastic strips in discrete sections onto a web of material for making diapers, comprising:

a drum having a toothed gear-like surface;

an embossing roller, having a tooth gear-like surface which is disposed for camming engagement with said drum and which in cooperation with said tooth gear-like surface of said drum serves to form a multiplicity of fine transverse folds in a web of material fed therebetween;

means for holding and guiding a gathered-up web of material on said drum; and means for mounting elastic strips in discrete sections onto the folded areas of the web of material which is held and guided on said drum.

6. The device according to claim 5, wherein said means for mounting said elastic strips comprises means for adhesively applying rubber band segments to said web.

7. The device according to claim 5, wherein said means for mounting said elastic strips comprises a spraying device.

8. The device according to claim 5, wherein said means for mounting said elastic strips comprises a casting device.

9. The device according to claim 5, wherein said means for holding and guiding comprises vacuum bores provided on said drum for an undistorted holding of the web of material on said drum, said vacuum bores being coupled by means of control devices with a vacuum source for a timed control of the vacuum.

10. The device according to claim 5, wherein said toothed gear-like surfaces of said drum and said embossing roller are defined by toothed gear belts.

11. The device according to claim 5, wherein said means for holding and guiding said web of material on said drum comprises at least one toothed gear belt surrounding said drum which has a width about equal to that of said web of material.

12. The device according to claim 10, wherein said toothed gear belt which forms the toothed gear-like surface of said embossing roller also travels around a large part of said drum.

13. The device according to claim 10, wherein said toothed gear belts which form the toothed gear-like surface of said drum and said embossing roller comprise a plurality of small adjacent toothed gear belts.

* * * * *